United States Patent
Some (10) Patent No.: US 8,195,405 B2
(45) Date of Patent: Jun. 5, 2012

(54) METHOD FOR CHARACTERIZING REVERSIBLE ASSOCIATION OF MACROMOLECULES AT HIGH CONCENTRATION

(75) Inventor: Daniel I. Some, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 435 days.

(21) Appl. No.: 12/459,437

(22) Filed: Jun. 30, 2009

(65) Prior Publication Data

US 2010/0332146 A1    Dec. 30, 2010

(51) Int. Cl.
*G06F 19/00* (2006.01)

(52) U.S. Cl. ........... 702/23; 702/25; 702/28; 250/559.4; 356/70; 356/73

(58) Field of Classification Search ............. 702/23, 702/25, 28; 250/559.4; 356/70, 73
See application file for complete search history.

(56) References Cited

U.S. PATENT DOCUMENTS

2009/0046274 A1 * 2/2009 McHugh et al. ............ 356/72

OTHER PUBLICATIONS

Kirkwood, J. G., and R. J. Goldberg, Light Scattering Arising from Composition Fluctuations in Multi-Component Systems, J. Chem. Phys., 1950, pp. 54-59, V. 18, No. 54, USA.

Minton, A., Static Light Scattering from Concentrated Protein Solutions, I: General Theory for Protein Mixtures . . . , Biophys. J., 2007, pp. 1321-1328, V. 93, USA.

Fernandez, C., and A. P. Minton, Static Light Scattering from Concentrated Protein Solutions II: Experimental Test . . . , Biophys. J., 2009, pp. 1992-1998, V. 96, USA.

Attri, A. K., A. P. Minton, Composition Gradient Static Light Scattering: A New Technique . . . , Analytical Biochemistry, 2005, pp. 132-138, V. 346, USA.

Wyatt Technology Corporation, Calypso promotional literature, 2009, Wyatt Technology Corporation, Goleta, USA.

Kirkwood, J. G., F. P. Buff, The Statistical Mechanlical Theory of Solutions. I, J. Chem Phys., 1951, pp. 774-777, V. 19, No. 6., USA.

* cited by examiner

*Primary Examiner* — Jonathan C Teixeira Moffat
*Assistant Examiner* — Hien Vo
(74) *Attorney, Agent, or Firm* — Philip J. Wyatt; David N. Villalpando (57) ABSTRACT

A new method is presented for characterizing the associative properties of a solution of macromolecules at high concentration. Sample aliquots spanning a range of concentrations are injected sequentially into a light scattering photometer. Equilibrium association constants and association stoichiometry are derived from an analysis of the angular and concentration dependence of the scattering signals. Thermodynamic nonideality, which becomes important at high concentrations, is dealt with in the analysis in a simplified manner which is applicable to multiple associated species.

30 Claims, 3 Drawing Sheets

METHOD FOR CHARACTERIZING REVERSIBLE ASSOCIATION OF MACROMOLECULES AT HIGH CONCENTRATION

BACKGROUND

Macromolecules, e.g. proteins, polysaccharides, synthetic polymers, etc., undergo different types of interactions in solution. Some of these interactions which are non-specific and repulsive are commonly referred to as 'thermodynamic non-ideality'. Some, whether specific or non-specific, are attractive and lead to reversible association, wherein the ratio of partial concentrations of monomer and associated complexes reaches an equilibrium state that depends on the overall concentration of the molecules in solution, the specific properties of the molecules, and the solvent. The reversible association state in turn impacts the functionality of the solution. For example, in the pharmaceutical industry, the presence of reversible antibody oligomers can increase solution viscosity, which adversely affects manufacture and delivery of therapeutics containing these antibodies. Oligomeric forms of an antibody drug may present an increased immunogenic risk. Determination of the association state, in the form of equilibrium association constants and association stoichiometries, of such macromolecules is an essential step in understanding and controlling the underlying interactions.

The standard methods for characterizing irreversible aggregates or tightly bound complexes in solution, such as size-exclusion chromatography (SEC), SEC in combination with multi-angle static light scattering (SEC-MALS), or sedimentation velocity (SV), are not applicable to weak reversible associations since these characterization techniques lead to dilution, dissociation of the complexes, and thus deviation from equilibrium.

Common methods known for characterizing strongly interacting reversible association include sedimentation equilibrium (SE), isothermal titration calorimetry (ITC), and composition gradient multi-angle static light scattering (CG-MALS). In SE, a solution of molecules is placed in an analytical ultracentrifuge and rotated at extremely high speed so as to form an equilibrium distribution which is recorded and analyzed. The specific shape of the distribution contains information on the amounts of self-associating monomer and complexes as well as the association stoichiometries. In ITC, the solution is titrated with respect to the solvent, in the case of self-association, or a solution initially containing only one macromolecule is titrated with respect to the second macromolecule, in the case of hetero-association, and the amount of heat given off or taken up by the solution is measured. This heat measurement and the corresponding shape of the titration curve, i.e. heat vs. titration volume and concentration, contain the requisite information on interaction strength and association stoichiometry, though typically only a single stoichiometry may be characterized. In CG-MALS, a series of dilutions is prepared and delivered to a MALS detector. The dependence of the scattered light intensity on concentration may be analyzed to determine association stoichiometries and equilibrium association constants. CG-MALS is a particularly useful technique since it does not require the very long equilibration times of sedimentation equilibrium. In addition, it is superior to ITC in determining associations resulting in multiple oligomeric states and simultaneous self- and hetero-association. When the associative interactions are strong, the solution is usually characterized at low concentration. However, when the associative interactions are weak, as is typically the case for antibody drug formulations, the solution must be characterized at high concentration, often in the range of 10-100 g/L.

At molecular concentrations above ~1 g/L, non-specific, typically repulsive interactions become significant and will affect the reversible association measurements of SE, ITC and CG-MALS. Hence characterization of weak association must often be carried out in a concentration range at which the non-specific interactions must also be accounted for in the analysis.

The theory describing static scattering of light by multiple species in solution subject to non-specific interactions, known as 'fluctuation theory', was described by Kirkwood and Goldberg in J. Chem. Phys. 18, 54-59 (1950). The application of fluctuation theory to light scattering under dilute conditions to a single non-associating species is well known, and involves only three parameters—the molar mass, mean square radius and second virial coefficient. As the solution concentration increases, higher-order virial coefficients must be included, making the analysis successively more difficult. A simplification described by Minton in Biophys. J. 93, 1321-1328 (2007), known as the 'effective hard sphere approximation' or EHSA, assumes that the non-specific interactions between molecules are equivalent to those of impenetrable spheres whose effective radii may differ from the actual radii of the molecules. The EHSA framework is useful in interpreting CG-MALS and other data at high concentrations of 10-150 g/L, which may otherwise be intractable. Fernandez and Minton, Biophysical J. 96, 1992-1998 (2009), have shown that fluctuation theory in combination with EHSA may be applied successfully to CG-MALS analysis of the reversible self-association of a protein to one or two oligomeric states at concentrations up to 70 g/L.

While the combined fluctuation/EHSA theory is rigorous, it becomes very complex mathematically if it must deal with more than two or three species that include monomers and complexes. Yet many important systems exhibit multiple stoichiometries of association, i.e. attain equilibrium between the monomers and several complexes simultaneously. One example is progressive self-association, forming dimer, trimer, tetramer, etc., up to high order oligomers. Another example is simultaneous self- and heteroassociation. Just writing out the full fluctuation theory equations for these cases is prohibitively difficult, let alone analyzing data in terms of the complex equation of Equation 1 below.

Hence a method for analyzing the reversible association of macromolecules at high concentration, using CG-MALS, which employs a more tractable representation of thermodynamic non-ideality yet accurately determines the sought for association constants and stoichiometries, would be advantageous.

SUMMARY OF THE INVENTION

This invention provides a method of representing CG-MALS data from a reversibly associating solution at high concentration in a highly tractable form amenable to simplified analysis of complex multiple stoichiometries.

In addition, using the inventive method provides for the determination of the equilibrium association parameters, i.e. the stoichiometry of associating complexes, the equilibrium association constants, and a measure of incompetent fractions present, of a macromolecular solution at high concentration via CG-MALS by means of the aforementioned tractable representation.

DETAILED DESCRIPTION OF THE INVENTION

Theoretical Description

The result of a generalized fluctuation theory for multi-component static light scattering, assuming that the incident light is vertically plane polarized and the observation is made in the horizontal plane at an angle $\theta$ relative to the direction of the incident light, is:

$$\frac{R(c_X, \theta)}{K} = \sum_{m,n} \left\{ \frac{\Psi_{m,n}(\theta) c_n M_m Q_{1,m,n}(\theta)}{|\psi_{m,n}(\theta)|} \left(\frac{dn}{dc_m}\right)\left(\frac{dn}{dc_n}\right) \right\}. \quad (1)$$

Here $R(c_X, \theta)$ represents the excess Rayleigh ratio detected at any scattering angle from a solution of macromolecules at a composition $c_X$, where X represents the various monomeric species and $c_X$ represents the totality of weight/volume concentrations $[c_1, c_2, c_3 \ldots]$ of each species; the excess Rayleigh ratio is the difference between the Rayleigh ratio of the solution and that of the pure solvent; the Rayleigh ratio of a solution is $$\frac{Ir_s^2}{Iv};$$

I is the intensity of scattered light per unit solid angle observed at a distance $r_s$ from the point of scattering due to an incident intensity I; v is the scattering volume;

$$K = \frac{(2\pi n_0)^2}{N_A \lambda_0^4};$$

$n_0$ is the refractive index of the solution; $N_A$ is Avogadro's number; $\lambda_0$ is the wavelength of the incident light in vacuum; m and n represent the different species present, including free monomers and complexes; $c_n$ is the weight concentration, in units of mass per unit volume, of the $n^{th}$ species; $Q_{1,m,n}$ is some function of the scattering angle $\theta$ which generally depends on the size and mass distributions within the m and n molecules, and approaches a value of 1 as either $\theta$ approaches zero or the overall size is much smaller than $$\frac{\lambda_0}{n_0}; \psi_{m,n}(\theta) = \delta_{m,n} + c_m \frac{\partial \ln \gamma_n}{\partial c_m} Q_{2,m,n}(\theta),$$

where $\delta_{m,n}$ equals 1 if m=n, and equals zero otherwise, $\gamma_n$ is the thermodynamic activity of component n, and $Q_{2,m,n}$ is some function of $\theta$ which generally depends on the size and mass distributions within the m and n molecules, and approaches a value of 1 as either $\theta$ approaches zero or the size is much smaller than $$\frac{\lambda_0}{n_0};$$

$|\psi_{m,n}(\theta)|$ is the determinant of $\psi_{m,n}(\theta)$; $\Psi_{m,n}(\theta)$ is the m,n cofactor, or subdeterminant, of $\psi_{m,n}(\theta)$; and $dn/dc_m$ is the differential refractive index increment of the $m^{th}$ species. If the $m^{th}$ species is a heterocomplex consisting of $i_X$ monomers of type X, $i_Y$ monomers of type Y, etc., then $dn/dc_m$ is the weight average of the contributing refractive index increments of the constituent molecules. The weight average of the refractive increment is $$\frac{\sum_X i_X M_X \frac{dn}{dc_X}}{\sum_X i_X M_X},$$

where the subscript X refers to the different constituent monomers. Equation (1) becomes very complex if more than two or three species are present, owing to the many terms incorporated in the determinant and subdeterminants.

The expression $$\frac{\partial \ln \gamma_n}{\partial c_m}$$

may be understood to represent the essential specific interaction volume $V^{interaction}/(M_m + M_n)$ between macromolecular species m and n that leads to thermodynamic non-ideality. Contributions to $$\frac{\partial \ln \gamma_n}{\partial c_m}$$

include the hard-core repulsion as well as various electrostatic and fluctuating dipole interactions. In a solution of at least intermediate ionic strength, long-range interactions are well-screened, and the non-ideality is dominated by short range interactions. At this condition the specific interaction volume is approximately proportional to the sum of the molecular volumes divided by the sum of masses, which may be written in terms of effective molecular density $\rho_m$:

$$\frac{\partial \ln \gamma_n}{\partial c_m} \propto \frac{M_m/\rho_m + M_n/\rho_n}{M_m + M_n}.$$

If the various species in solution are formed as oligomers of just one type of monomer self-associating to form i-mers, then we may reasonably expect that the effective density of all i-mers is approximately a constant $\rho$, so $$\frac{\partial \ln \gamma_n}{\partial c_m} \propto \frac{1}{\rho}$$

is independent of m or n.

$$\frac{\partial \ln \gamma_n}{\partial c_m}$$

is commonly approximated as a series in powers of the concentration:

$$\frac{\partial \ln \gamma_m}{\partial c_m} \cong \frac{\partial \ln \gamma_1}{\partial c_1} = 2A_2 M + 3A_3 M c_m + \ldots \quad$$

where the coefficients $A_2$ and $A_3$ are known as the second and third virial coefficients of the monomer in the particular solvent, respectively. Applying this approximation, Eq. (1) may be reduced to a simplified form heretofore unknown in the scientific literature, wherein all the non-ideal self- and cross-interactions are captured in just the two parameters $A_2$ and $A_3$:

$$\frac{R(c,\theta)}{K} = \left(\frac{dn}{dc}\right)^2 \frac{\sum_i i M c_i P_i(\theta)}{1 + 2A_2 M \sum_i c_i P_i(\theta) + 3A_3 M \sum_i c_i^2}. \quad (2)$$

Here $R(c, \theta)$ is the excess Rayleigh ratio observed at azimuth angle $\theta$ and a total macromolecular concentration $c$; $M$ is the molar mass of the monomer; $dn/dc$ is the differential refractive index increment of the molecules in the solvent; $i$ is the order of self-association; $c_i$ is the weight concentration at equilibrium of the i-mer; $\langle r_g^2 \rangle_i$ is the angular dependence of the scattered light, within the plane perpendicular to the vertically polarized incident light, for the i-mer; $\theta$ is measured relative to the direction of propagation of the beam; and $\langle r_g^2 \rangle_i$ is the mean square radius of the i-mer defined as $\langle r_g^2 \rangle_i = \int r^2 dm_i / \int dm_i$ where $r$ is the distance from the center of mass of the molecule to a molecular mass element $m_i$, integrated over all mass elements of the molecule. The validity of Eq. (2) may be illustrated with a relatively simple example as follows:

For two species—a monomer and one i-mer, $$|\psi_{m,n}(\theta)| = \left(1 + c_1 \frac{\partial \ln \gamma_1}{\partial c_1}\right)\left(1 + c_i \frac{\partial \ln \gamma_i}{\partial c_i}\right) - c_1 c_i \frac{\partial \ln \gamma_i}{\partial c_1} \frac{\partial \ln \gamma_1}{\partial c_i}$$

$$= 1 + c_1 \frac{\partial \ln \gamma_1}{\partial c_1} + c_i \frac{\partial \ln \gamma_i}{\partial c_i} + c_1 c_i \left(\frac{\partial \ln \gamma_1}{\partial c_1} \frac{\partial \ln \gamma_i}{\partial c_i} - \frac{\partial \ln \gamma_i}{\partial c_1} \frac{\partial \ln \gamma_1}{\partial c_i}\right)$$

Each of the terms $$\frac{\partial \ln \gamma_n}{\partial c_m} \propto \frac{1}{\rho}.$$

Hence the term $$c_1 c_i \left(\frac{\partial \ln \gamma_1}{\partial c_1} \frac{\partial \ln \gamma_i}{\partial c_i} - \frac{\partial \ln \gamma_i}{\partial c_1} \frac{\partial \ln \gamma_1}{\partial c_i}\right)$$

is not only of higher order than the other terms, it is the difference of two quantities that are of comparable magnitude, and hence should be small compared to even one second-order term. It will also be small as one of the concentrations tends to zero. The final expression for the denominator will be $$|\psi_{m,n}(\theta)| \approx 1 + c_1 \frac{\partial \ln \gamma_1}{\partial c_1} + c_i \frac{\partial \ln \gamma_i}{\partial c_i}.$$

Likewise, for any number of species, the higher order terms may be ignored to yield $$|\psi_{m,n}(\theta)| \approx 1 + \sum_m c_m \frac{\partial \ln \gamma_m}{\partial c_m}$$

The $$\frac{\partial \ln \gamma_m}{\partial c_m}$$

may be expressed in terms of virial coefficients as described above, with the approximation that $A_2 M$ and $A_3 M$, which are closely related to the inverse density, are approximately constants for the monomer and all oligomers:

$$|\psi_{m,n}(\theta)| \approx 1 + (2A_2 M P_1(\theta) + 3A_3 M c_1 + \ldots)c_1 +$$
$$(2A_2 M P_i(\theta) + 3A_3 M c_i + \ldots)c_i + \ldots =$$
$$1 + 2A_2 M \sum_i c_i P_i(\theta) + 3A_3 M \sum_i c_i^2 + \ldots$$

Also, for two species, monomer and one i-mer, $$\frac{dn}{dc_1} = \frac{dn}{dc_i}$$

so that the numerator of Eq. (1) becomes:

$$\left[M c_1 P_1(\theta)\left(1 + c_i \frac{\partial \ln \gamma_i}{\partial c_i}\right) + i M c_i P_i(\theta)\left(1 + c_1 \frac{\partial \ln \gamma_1}{\partial c_1}\right) - \right.$$
$$\left. c_1 c_i \left(i M P_i(\theta) \frac{\partial \ln \gamma_1}{\partial c_i} + M P_1(\theta) \frac{\partial \ln \gamma_i}{\partial c_1}\right)\right]\left(\frac{dn}{dc_1}\right)^2 =$$
$$\left[M c_1 P_1(\theta) + i M c_i P_i(\theta) + c_1 c_i \left(M P_1(\theta) \frac{\partial \ln \gamma_i}{\partial c_i} + i M_i P_i(\theta) \frac{\partial \ln \gamma_1}{\partial c_1} - \right.\right.$$
$$\left.\left. i M P_i(\theta) \frac{\partial \ln \gamma_1}{\partial c_i} - M P_1(\theta) \frac{\partial \ln \gamma_i}{\partial c_1}\right)\right]\left(\frac{dn}{dc_1}\right)^2 \approx$$
$$[M c_1 P_1(\theta) + i M c_i P_i(\theta)]\left(\frac{dn}{dc_1}\right)^2$$

as again there is a term which includes the difference of high-order terms of very comparable magnitude and so may be ignored. Likewise, for any number of oligomeric species, the final expression would be $$\sum_m m M c_m P_m(\theta)\left(\frac{dn}{dc_1}\right)^2$$

Combining these approximations for the numerator and denominator of Eq. (1) yields Eq. (2). Numerical studies show that the terms that have been dropped only account for a small fraction of the total non-ideality correction, up to concentrations of tens of g/L, and thus the relationships that are the subject of this invention are applicable at such high concentrations.

Under certain common assumptions, a fixed relationship may be assumed between $A_2$ and $A_3$, so that a single parameter captures all the non-ideal behavior. For example, if the molecules are assumed to behave like hard spheres then $$A_3 = \frac{5}{8} A_2^2 M.$$

Depending on the relative magnitudes of $A_2$, $A_3$ and the $\sin^2(\theta/2)$ terms in the $P_j$, some of the terms in Eq. (2) may be ignored, as will be obvious to those familiar with numerical analysis. For example, for molecules in a solution of only moderately high concentration $A_3$ may be ignored, and if the complexes are all smaller than about $\lambda/70$, the angular dependence may be ignored as well, yielding a very simple form:

$$\frac{R(c)}{K} = \left(\frac{dn}{dc}\right)^2 \frac{\sum_i i M c_i}{1 + 2 A_2 M c^{tot}} \quad (3)$$

where $$c^{tot} = \sum_i c_i$$

is the total weight/volume concentration of the material in solution.

If the various species in solution are formed as complexes of two different monomers X and Y, then under similar assumptions to those stated above, Eq. (1) may be reduced to a highly simplified form heretofore unknown in the scientific literature, wherein all the non-ideal self- and cross-interactions are captured in just two parameters $A_2^X$ and $A_2^Y$:

$$\frac{R(c, \theta)}{K} = \frac{\sum_{i,j}\left[\left(iM_X \frac{dn}{dc_X} + jM_Y \frac{dn}{dc_Y}\right)^2 \frac{c_{ij} P_{ij}(\theta)}{M_{ij}}\right]}{1 + 2A_2^X M_X \sum_{ij} \frac{iM_X c_{ij} P_{ij}(\theta)}{M_{ij}} + 2A_2^Y M_Y \sum_{ij} \frac{jM_Y c_{ij} P_{ij}(\theta)}{M_{ij}}} \quad (4)$$

where $M_X$ and $M_Y$ correspond to the molar masses of the X and Y monomers; $dn/dc_X$ and $dn/dc_Y$ correspond to the differential refractive index increments of the X and Y monomers in the particular solvent; i and j are the number of X and Y monomers in the complex, $M_{ij} = iM_X + jM_Y$ is the molar mass and $c_{ij}$ is the weight concentration, at equilibrium, of the XiYj complex; $A_2^X$ and $A_2^Y$ refer to the second virial coefficients of the X and Y monomers in the particular solvent;

$$P_{ij}(\theta) = 1 - \frac{16\pi^2 n_0^2}{3\lambda_0^2} \langle r_g^2 \rangle_{ij} \sin^2(\theta/2) + \ldots$$

and $\langle r_g^2 \rangle_{ij}$ is the mean square radius of the ij complex. The derivation is similar to that described for oligomers of the same monomer.

If the complexes are smaller than about $\lambda/70$ then the angular dependence may be ignored and Eq. (4) may be reduced to:

$$\frac{R(c)}{K} = \frac{\sum_{i,j}\left[\left(iM_X \frac{dn}{dc_X} + jM_Y \frac{dn}{dc_Y}\right)^2 \frac{c_{ij}}{M_{ij}}\right]}{1 + 2A_2^X M_X c_X^{tot} + 2A_2^Y M_Y c_Y^{tot}} \quad (5)$$

where $$c_X^{tot} = \sum_{ij} \frac{iM_X c_{ij}}{M_{ij}}$$

and $$c_Y^{tot} = \sum_{ij} \frac{jM_Y c_{ij}}{M_{ij}}$$

are the total weight/volume concentrations of X and Y in solution. Equations (4) and (5) may be readily generalized to more than two distinct monomeric species.

Determining $A_2$

The non-ideality parameter $A_2$ may be estimated a priori, or it may be a parameter of the fit of the data to the non-ideality-corrected light scattering equation and the association model equations described below.

In order to estimate $A_2$ from a priori information, a known molecular radius may be substituted into the formula for computing $A_2$ of a hard sphere:

$$A_2 = \frac{16\pi N_A}{3} \frac{r^3}{M^2}.$$

The molecular radius of the monomer may be derived from structural information, e.g. as may be determined by x-ray crystallography, or estimated from a measurement of the hydrodynamic radius $r_h$. The hydrodynamic radius may be calculated from measurements of dynamic light scattering or differential viscometry under dilute conditions, as is known to those familiar with macromolecular characterization.

Methods for Simplified Representations of Non-Ideal Solutions

Figure 1:
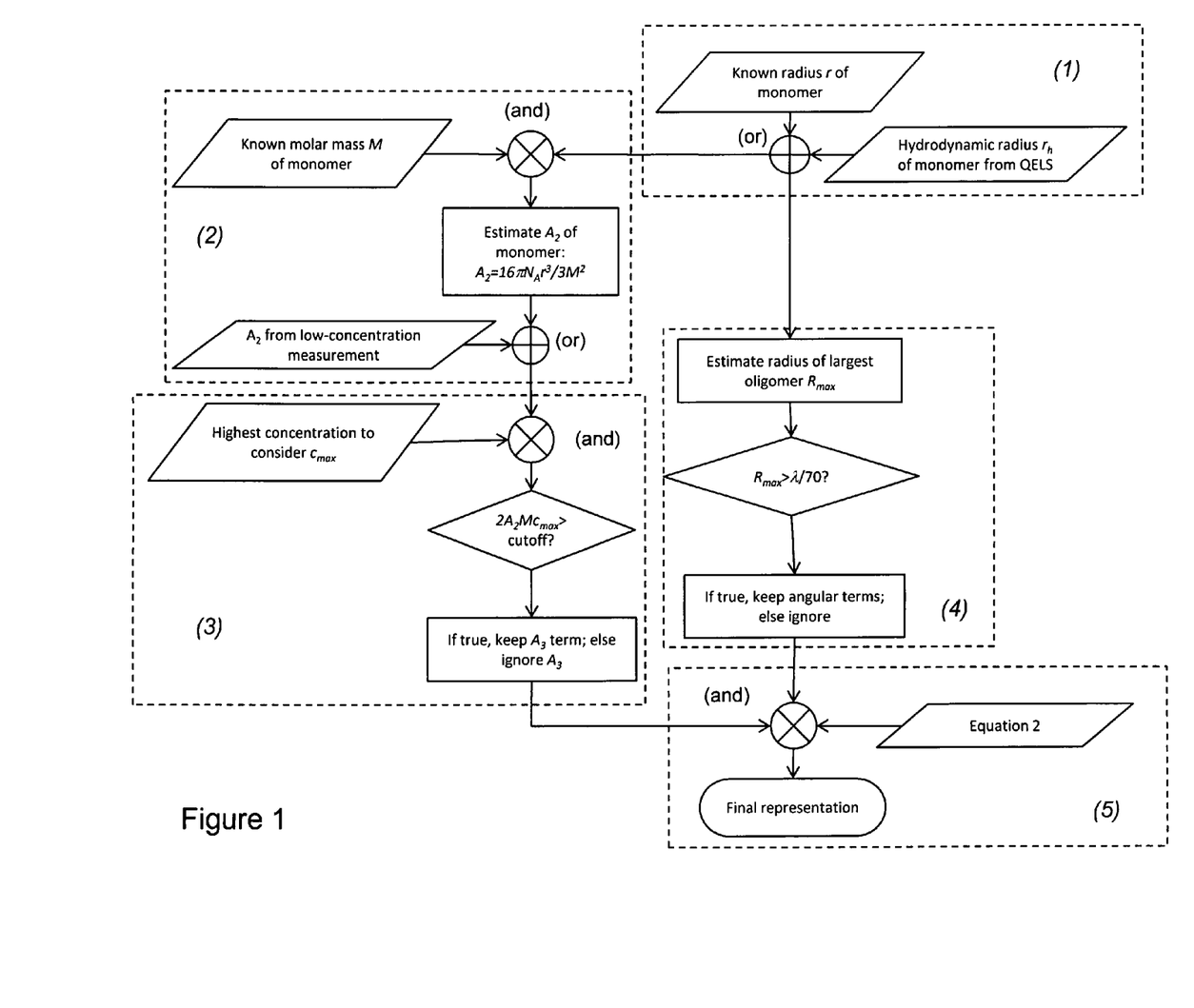
FIG. 1 is a flow diagram of a method for representing the non-ideality of a solution of a reversibly self-associating species.

Hence one method for representing CG-MALS data from a reversibly self-associating solution at high concentration, in a highly simplified form amenable to further analysis, consists of the following steps as illustrated in FIG. 1:

1. Determine a suitable estimate of the effective molecular radius r either from the known structure of the molecule, or from a quasi-elastic light scattering or differential viscometry measurements of the hydrodynamic radius $r_h$ taken under non-associating conditions such as suitably low concentration or an appropriate association-restricting solvent;
2. Based on the known molar mass of the monomer M and the estimated effective molecular radius r, estimate the monomer excluded volume value $$A_2 = \frac{16\pi N_A r^3}{3M^2}.$$

In some cases, the association is relatively weak and it is possible to estimate $A_2$ from a series of measurements at low concentrations.

3. Given the maximal concentration of interest $c_{max}$, compute an estimate of the maximum non-ideality contribution $\xi = 2A_2Mc_{max}$; if $\xi$ is greater than a predetermined cutoff value, e.g. 0.3, retain the $A_3$ term in Eq. (2); otherwise, drop the $A_3$ term;

4. Estimate the mean square radius $r_{max}$ of the largest oligomer expected to form; if $r_{max} > \lambda/70$, retain the angular terms in Eq. (2); otherwise, drop them.

5. Use the final form of Eq. (2) to represent the CG-MALS data. If some of the macromolecules are expected to be incompetent to reversible association, treat it in the equation as a distinct species that does not associate but has the same virial coefficient as the competent macromolecules.

Figure 2:
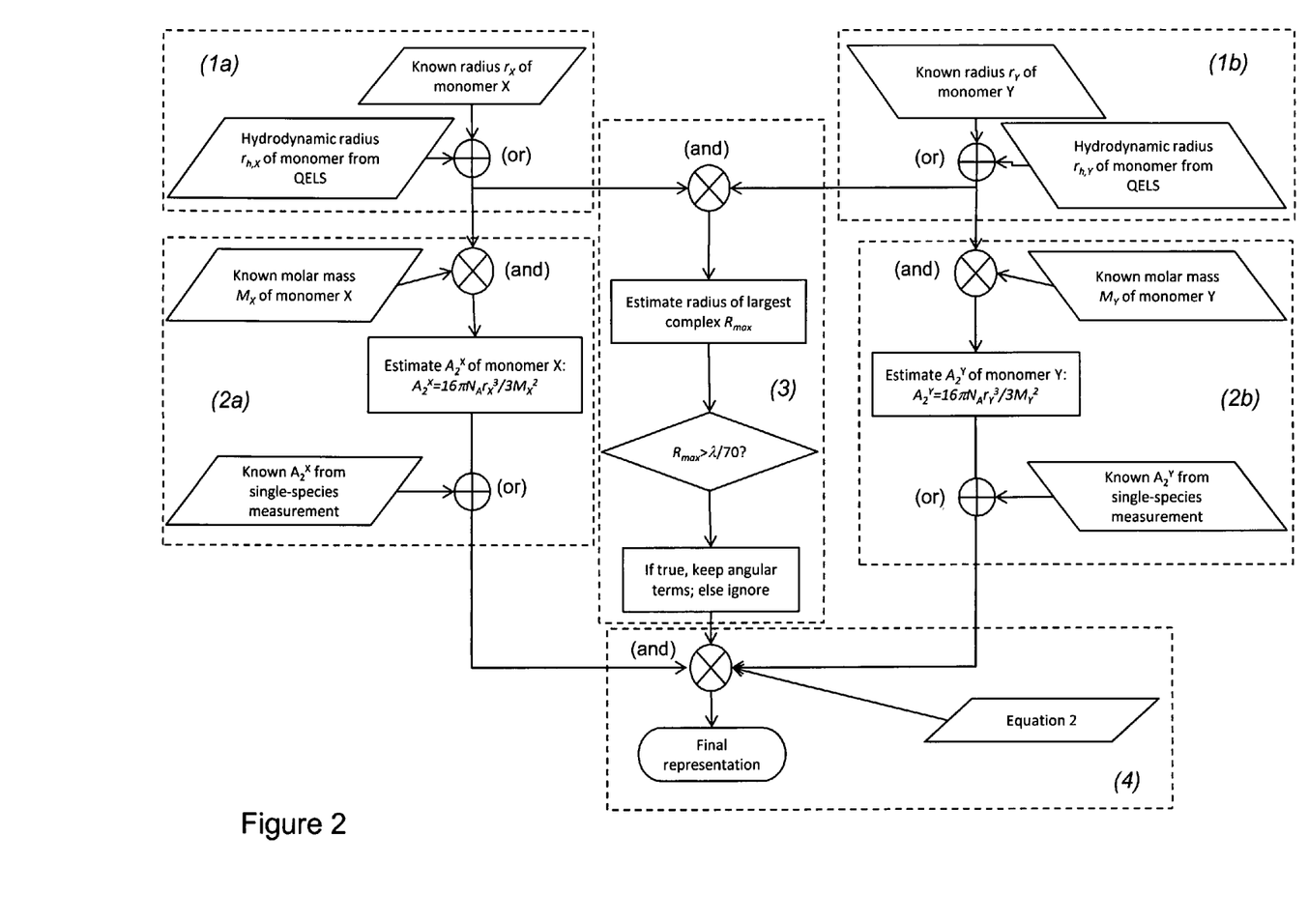
FIG. 2 is a flow diagram of a method for representing the non-ideality of a solution of two constituent species forming reversible complexes.

A method for representing CG-MALS data from a reversibly hetero-associating solution at high concentration, in a highly simplified form amenable to further analysis, consists of the following steps as illustrated in FIG. 2:

1. Determine a suitable estimate of the effective molecular radii $r_X$ and $r_Y$ either from the known structure of the molecule, or from quasi-elastic light scattering or differential viscometry measurements of the hydrodynamic radii $r_{h,X}$ and $r_{h,Y}$;

2. Based on the known molar masses of the monomers $M_X$, $M_Y$ and the estimated effective molecular radii $r_X$ and $r_Y$, estimate the monomer excluded volume values $$A_{2,X} = \frac{16\pi N_A r_X^3}{3M_X^2}, A_{2,Y} = \frac{16\pi N_A r_Y^3}{3M_Y^2}.$$

In some cases, the association is relatively weak and it is possible to estimate $A_2$ from a series of measurements at low concentrations.

3. Estimate the mean square radius $r_{max}$ of the largest complex expected to form; if $r_{max} > \lambda/70$, retain the angular terms in Eq. (4); otherwise, drop them.

4. Use the final form of Eq. (4) to represent the CG-MALS data. If some of the macromolecules are expected to be incompetent to reversible association, treat them in the equation as a distinct species that does not associate but has the same virial coefficient as the competent macromolecules.

Variants on these methods for determining suitable forms of the above equations will be apparent to those familiar with numerical analysis.

Methods for Characterizing Reversibly Associating Non-Ideal Solutions

With thermodynamic non-ideality accounted for in a simplified equation according to one of the forms shown above, characterization of the interaction in terms of stoichiometry and equilibrium association constants is straightforward and similar to the methods described by Attri and Minton in Anal. Biochem. 346, 132-138 (2005) for ideal solutions and by Fernandez and Minton in Biophys. J. 96, 1992-1998 (2009) for concentrated solutions, but employing Eq. (1) rather than one of the simplified forms described herein.

The characterization method comprises the steps of: preparing a series of solutions comprising one or more macromolecular species; allowing each solution to reach equilibrium between the free monomers and any reversibly-associating complexes; measuring the light scattering intensity of each solution; reducing the light scattering data to a series of excess Rayleigh ratios; and fitting the data simultaneously to the appropriate simplified representation of non-ideal light scattering and the equations for the specific association model described below.

The model equations for self-association are:

1. the equations for mass action, relating each equilibrium oligomer concentration $c_i$ to the corresponding equilibrium association constant $K_i$ for the specific stoichiometry, and the concentration of free monomer $c_1$:

$$\frac{c_i}{iM} = K_i \left(\frac{c_1}{M}\right)^i;$$

2. the equation for conservation of mass $$c^{tot} = \sum_i c_i + c^{inc}$$

where $c^{tot}$ is known for each solution as determined by the preparation procedure or measured by a concentration detector, and $c^{inc}$ is the concentration of macromolecules incompetent to associate and is considered a distinct species.

The model equations for heteroassociations of two different monomer species X and Y are:

1. the equations for mass action, relating each equilibrium complex concentration $c_{ij}$ to the corresponding equilibrium association constant $K_{ij}$ for the specific stoichiometry, and the concentration of free monomer $c_X$, $c_Y$:

$$\frac{c_{ij}}{iM_X + jM_Y} = K_{ij}\left(\frac{c_X}{M_X}\right)^i\left(\frac{c_Y}{M_Y}\right)^j;$$

2. the equations for conservation of mass $$c_X^{tot} = \sum_{i,j}\left(\frac{iM_X}{iM_X + jM_Y}\right)c_{i,j} + c_X^{inc}, c_Y^{tot} = \sum_{i,j}\left(\frac{jM_Y}{iM_X + jM_Y}\right)c_{i,j} + c_Y^{inc}$$

where $c_X^{tot}$ and $c_Y^{tot}$ are known for each solution as determined by the preparation procedure or measured with concentration detectors; and $c_X^{inc}$ and $c_Y^{inc}$ are the concentrations of X and Y macromolecules, respectively, incompetent to associate, and considered additional distinct species.

Various fitting algorithms, such as Levenberg-Marquardt nonlinear least squares algorithms and others, are well known from numerical analysis theory. These algorithms may be employed for fitting the data to the system of equations which includes the non-ideal light scattering equation, the mass conservation equations and the mass action equations, thereby obtaining fitted values of the interaction parameters $K_i$ or $K_{ij}$, $A_2$, etc.

Measurement Apparatus and Procedure—Self-Association

Figure 3:
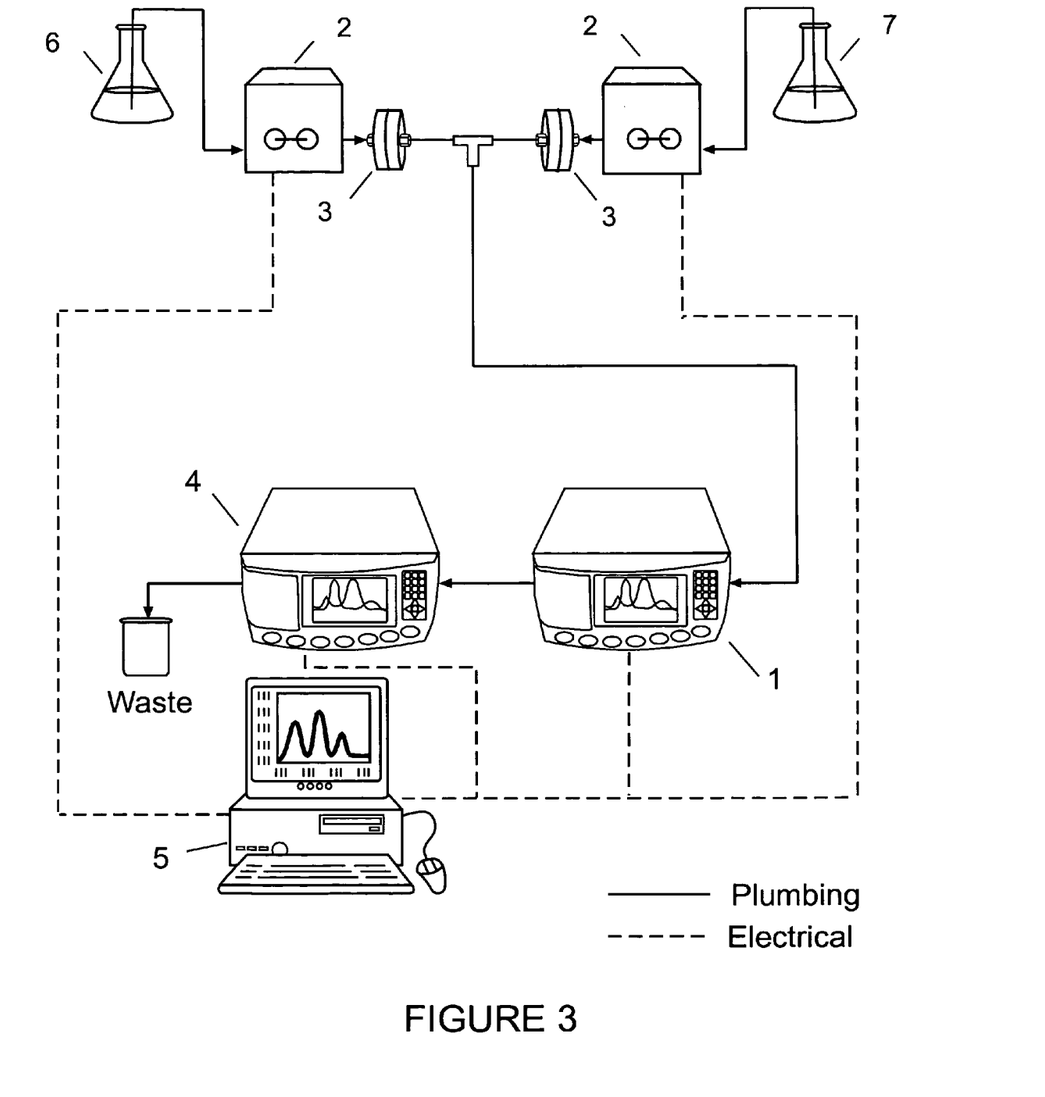
FIG. 3 is a schematic of an apparatus used in determining the equilibrium association parameters of one or more species undergoing reversible association.

Referring to FIG. 3, a set of aliquots of the macromolecule of interest, at concentrations $c_1, c_2, \ldots c_k$, are introduced into MALS detector 1, providing photodetectors at a plurality of scattering angles $\theta_v$. One example of a MALS detector is the DAWN-HELEOS®, from Wyatt Technology Corporation, Santa Barbara, Calif.

In a typical procedure, the concentration series corresponds to $c_s = \alpha \Delta c$, where $s = 1, 2, \ldots k$; $\Delta c$ is a fixed concentration step, and k is the number of concentrations, usually at least five. Aliquots of each of the k concentrations may be prepared and introduced to the detectors by means of various methods. In one method, these aliquots are prepared manually and placed in the MALS detector by means of scintillation vials or cuvettes. In a second method, the aliquots are prepared manually and injected into the light scattering detector flow cell by means of a pump 2. In a third method, the aliquots are prepared automatically by means of a dual pump 2 under computer control, which dilutes a stock solution 6 at a maximal concentration $c^{max}$ with a solvent 7, and subsequently delivers sequentially each aliquot as produced to the detector. One example of an extant system capable of carrying out the dilution and delivery are the Calypso™ SP3 accessory using the Calypso™ software, from Wyatt Technology Corporation, Santa Barbara, Calif.

The actual concentrations of the aliquots in the flow cell may differ from the original, as-prepared values $c_s$, as the sample dilutes in the course of flowing through the system and interacting with filters 3, surfaces, etc. A sufficient injection volume will fully equilibrate the detector flow cell at each injected concentration, so that knowledge of the as-prepared concentrations $c_s$ suffices to determine the actual concentration in the MALS flow cell. Alternatively, the optional in-line concentration detector 4 may be used to measure the actual sample concentrations.

Various methods are known for determining the concentration of a sample in solution. In one method applicable to manual preparation of the aliquots, appropriate masses of concentrated or lyophilized sample are weighed out and dissolved in a known volume of the solvent. In a second method, the concentration is determined by measuring absorbance with a spectrophotometer. In a third method, the concentrations are determined by means of a suitable in-line concentration detector 4 connected in series with the MALS detector. An example of an in-line concentration detector is the Optilab® rEX™, also from Wyatt Technology Corporation; other in-line concentration detectors are known, including UV/V is absorption and fluorescence detectors. The in-line concentration detector may be connected in series or in parallel with the MALS detector. If the MALS and concentration detectors are connected in series, a sufficient volume of sample must be delivered so as to saturate both flow cells at the desired concentration. If the MALS and concentration detectors are connected in parallel, then the sample flow must be split between them in a controlled fashion so as to ensure that at the completion of each sample injection, the concentrations in the two detectors are the same. Sample flow splitting is typically controlled by a needle valve and monitored by means of suitable flow meters so as to maintain the required ratio.

Data is acquired from the detectors while the sample is flowing and while it is stopped between injections, then stored and analyzed by a computer 5 performing the fitting procedure described previously. Optimally the data to be used for the analysis is that acquired after flow has stopped and the sample has equilibrated.

Each successive sample passes through the MALS detector 1, whereby the values of the excess Rayleigh ratio, $R_s(c_s, \theta_v)$, at each detector angle $\theta_v$, are measured at successive sample concentrations $c_s$. The resultant light scattering and concentration signals are then stored and processed by a computer means 5 to calculate, for each injected aliquot s, the values $c_s$, $R_s(c_s, \theta_v)$. Computer 5 also computes the molecular characteristics including M and $<r_g^2>$, and the molecular interaction characteristics $A_2$ and $K_i$, by fitting the calculated results to Eq. (2) or a simplified form thereof, together with the association model equations. Various fitting procedures may be implemented to extract the molecular interaction characteristics. In a preferred embodiment, the fitting procedure consists of the Levenberg-Marquardt algorithm as applied to two variables (c and $\sin^2(\theta/2)$), with M and $A_2$ fixed.

From numerical analysis theory, the fitting of the measured data to the form of the light scattering equation and association model equations, whether by the Levenberg-Marquardt method, or other algorithms, may include statistical weighting whereby the data used to perform these fits is weighted by their reciprocal measured standard deviations.

Measurement Apparatus and Procedure—Heteroassociation

The measurement proceeds as for a single-species measurement, except that each aliquot contains different concentrations of two macromolecular species X and Y in various association states to be determined.

In one procedure, known as a crossover composition gradient, k aliquots are prepared wherein the composition of the $s^{th}$ aliquot is $[s\Delta c_X, (k-s)\Delta c_Y]$, and $\Delta c_X$ and $\Delta c_Y$ are fixed concentration step sizes.

In another procedure, known as a constant-ratio composition gradient, k aliquots are prepared wherein the composition of the $s^{th}$ aliquot is $[s\Delta c_X, s\Delta c_Y]$, and $\Delta c_X$ and $\Delta c_Y$ are fixed concentration step sizes.

The apparatus is similar to those of the single-species measurement, except that a computer-controlled triple-pump system is employed instead of a dual pump system, each pump controllable by means of computer to produce, mix and deliver an aliquot comprising species X, species Y, and solvent at the desired compositions. Such a triple-pump system and suitable controlling software are the Calypso system, of Wyatt Technology Corporation, Santa Barbara, Calif.

The total concentrations of constituents X and Y, $c_X^{tot}$ and $c_Y^{tot}$ respectively, may be determined from the predetermined stock solution concentrations and the mixing ratio as set in the preparation method, or by means of a method for measuring concentrations of two species in solution.

In one method for measuring the concentrations of two distinct molecules in solution, the total concentration signal is measured by means of an on-line concentration detector 4, and the constituent concentrations calculated from the known ratio between the two constituent species and the relative contributions of each to the total concentration signal. Such a method has been described by Attri and Minton in Anal. Biochem. 346 (2005) 132-138.

In a second method for measuring the concentrations of two distinct molecules in solution, at least two different on-line concentration detection means are used, and the constituent concentrations determined from the concentration signals and the known responses of each constituent species to each concentration detection means. For example, the signals of a differential refractometer and UV absorption detector may be analyzed to yield the concentrations of each of two species present in the same solution, if the responses of the molecules to the respective concentration detectors differs for at least one measurement.

As will be evident to those skilled in the arts of light scattering, macromolecular characterization, and numerical analysis, there are many obvious variations of the methods we have invented and described that do not depart from the fundamental elements that we have listed for their practice; all such variations are but obvious implementations of the invention described hereinbefore and are included by reference to our claims, which follow.

What is claimed is:

1. A method for determining values of equilibrium association constants, stoichiometries of association, incompetent fractions, second and third virial coefficients, and/or molar masses corresponding to self-association of reversibly associating macromolecules in solution at high concentration in a solvent, comprising the steps of:
   1. introducing a series of k aliquots of solutions of the molecule of interest at concentrations $c_f$, $f=1\ldots k$ of into a light scattering photometer, whereby said light scattering photometer
      i. illuminates each injected diluted aliquot by a light beam and
      ii. detects the intensity of light scattered therefrom at one or more angular locations $\theta$ at which is placed a light sensitive detector;
   2. determining the concentration $c_f$ of each diluted aliquot f;
   3. forming the excess Rayleigh ratios $R(c_f, \theta)$ from said detected scattered light intensities;
   4. representing said excess Rayleigh ratios to correct for thermodynamic non-ideality in terms of said k dilutions $c_f$, $f=1\ldots k$ as $$\frac{R(c_f, \theta)}{K} = \left(\frac{dn}{dc}\right)^2 \frac{\sum_i iMc_{f,i}P_i(\theta)}{1 + 2A_2Mc_f\left(c_f - \frac{16\pi^2}{3\lambda^2}\sum_i c_{f,i}\langle r_g^2\rangle_i \sin^2(\theta/2)\right) + 3A_3M\sum_i (c_{f,i})^2},$$

wherein M is the molar mass of the monomer, i the order of each self-associating i-mer, $c_{f,i}$ the partial equilibrium concentration of the i-mer in the $f^{th}$ diluted aliquot, $$P_i(\theta) = 1 - \frac{16\pi^2}{3\lambda^2}\langle r_g^2\rangle_i \sin^2(\theta/2),$$

$\lambda$ is the wavelength of said illuminating light beam, $\langle r_g^2\rangle_i$ the mean square radius of the i-mer, $$K = \frac{4\pi^2 n^2}{N_A \lambda^4},$$

n the refractive index of said solution, $N_A$ Avogadro's number, and dn/dc the refractive increment of said macromolecule in said solution;
   5. fitting said representations of said excess Rayleigh ratios to the equations of an association model; and
   6. determining from said fitted representations the values of equilibrium association constants, stoichiometries of association, incompetent fractions, second and third virial coefficients, and/or molar masses.

2. The method of claim 1 further comprising the steps of
   a. estimating the value of the molecular radius r from a derived molecular structure; and
   b. estimating $A_2$ as the excluded volume value, $$\frac{16\pi N_A r^3}{3M^2},$$

based on said estimated value of molecular radius.

3. The method of claim 1 further comprising the steps of
   a. determining the hydrodynamic radius of said macromolecules in solution by means of dynamic light scattering, differential viscometry or similar experimental techniques;
   b. estimating the molecular radius r corresponding to said determined hydrodynamic radius; and
   c. estimating $A_2$ as the excluded volume value, $$\frac{16\pi N_A r^3}{3M^2},$$

based on said estimated value of molecular radius.

4. The method of claim 1 further comprising the step of assuming the third virial coefficient $A_3$ is negligible, and therefore setting its value to zero.

5. The method of claim 1 further comprising the step of assuming said mean square radii of complexes of said macromolecules in solution are $<\lambda/70$, where $\lambda$ is the wavelength of said light beam of said light scattering photometer, and thereby the angular dependence of said intensity of scattered light may be ignored, and therefore said intensity may be measured at only one angle, $P(\theta)=1$, and $\langle r_g^2\rangle_{ii}$ terms are considered negligible and therefore set to zero for all i-mers.

6. The method of claim 1 further comprising the step of assuming said mean square radii of complexes of said macromolecules in solution are $<\lambda/70$, where $\lambda$ is the wavelength of said light beam of said light scattering photometer, and thereby the angular dependence of said intensity of scattered light may be ignored, and therefore said intensity may be measured at only one angle, $P(\theta)=1$, and therefore $\langle r_g^2\rangle_{ii}$ is set to zero for all i-mers in the denominator only of $R(c_f, \theta)$.

7. The method of claim 1 wherein said aliquots are prepared manually and introduced to the detectors by means of scintillation vials.

8. The method of claim 1 wherein said aliquots are prepared manually and introduced to the detectors by means of a pump.

9. The method of claim 1 wherein said aliquots are prepared and introduced to the detectors automatically by means of a dual pump diluting a stock solution at the highest required concentration.

10. The method of claim 1 wherein said determining of said concentrations of comprises:
    a. placing a concentration detector in-line with the light scattering photometer;
    b. injecting a diluted aliquot of sufficient volume so as to fill the flow cells of both the light scattering photometer and the concentration detector;
    c. detecting the signal from said concentration detector; and
    d. converting the signal to concentration based on the known response factor of the macromolecule.

11. The method of claim 1 wherein said determining of said concentrations of comprises
    a. measuring the concentration of the said high concentration solution in a concentration detector;
    b. calculating the concentrations $c_j$ of each diluted aliquot from the parameters of the dilution procedure.

12. The method of claim 1 wherein said concentration detector comprises a UV/Visible light absorbance photometer, and said response factor is the absorption coefficient.

13. The method of claim 1 wherein said concentration detector comprises a differential refractometer, and said response factor is the refractive increment.

14. The method of claim 1 wherein said representations of said excess Rayleigh ratios are fitted to said equations of an association model by means of a Levenberg-Marquardt non-linear least-squares fit.

15. A method for characterizing hetero-association of two reversibly associating macromolecular species in solution at high concentration in a solvent, comprising the steps of:
1. preparing reservoirs containing high concentration solutions of each macromolecular species and another reservoir containing said solvent;
2. preparing a series of k composition aliquots $[c^x_f, c^Y_f]$, f=1 . . . k of said high concentration solution by mixing aliquots of said high-concentration solutions and said solvent, wherein each composition aliquot comprises macromolecule X at concentration $c^x_f$ and macromolecule Y at concentration $c^Y_f$,
3. injecting sequentially said composition aliquots into a light scattering photometer, whereby said light scattering photometer
   i. illuminates each injected dilution by a light beam; and
   ii. detects the intensity of light scattered therefrom at one or more angular locations at which is placed a light sensitive detector;
4. determining the composition $[c^x_f, c^Y_f]$ of each composition aliquot f by means of a concentration detector and the response factor of said macromolecules in said solution;
5. forming the excess Rayleigh ratios $R(c^x_f, c^Y_f, \theta)$ from said detected scattered light intensities;
6. representing said excess Rayleigh ratios to correct for thermodynamic non-ideality in terms of said k dilutions $c_f$, f=1 . . . k as $$\frac{R(c^X_f, c^Y_f, \theta)}{K} = \frac{\sum_{i,j}\left[\left(iM_X \frac{dn}{dc_X} + jM_Y \frac{dn}{dc_Y}\right)^2 \frac{c_{f,ij} P_{ij}(\theta)}{M_{ij}}\right]}{1 + 2A^X_2 M_X \sum_{ij} \frac{iM_X c f_{,ij} P_{ij}(\theta)}{M_{ij}} + 2A^Y_2 M_Y \sum_{ij} \frac{jM_Y c f_{,ij} P_{ij}(\theta)}{M_{ij}}},$$

wherein M is the molar mass of the monomer, i and j the stoichiometry ratios of the XiYj complex, $c_{f,ij}$ the partial equilibrium concentration of the XiYj complex at the f$^{th}$ composition aliquot, $$P_{ij}(\theta) = 1 - \frac{16\pi^2}{3\lambda^2}\langle r^2_g\rangle_{ij} \sin^2(\theta/2),$$

$\lambda$ is the wavelength of said illuminating light beam, $\langle r_g^2\rangle_{ij}$ the mean square radius of the XiYj complex, $$K = \frac{4\pi^2 n^2}{N_A \lambda^4},$$

n the refractive index of said solution, $N_A$ Avogadro's number, and $dn/dc_x$ and $dn/dc_y$ the refractive increments of said macromolecules X and Y in said solution; and 7. fitting said representations of said excess Rayleigh ratios to the equations of an association model in order to determine some or all of equilibrium association constants, stoichiometries of association, incompetent fractions, second virial coefficients and molar masses.

16. The method of claim 15 further comprising the steps of
a. estimating the values of the molecular radii $r_x$ and $r_y$ from their derived molecular structures; and
b. estimating $A_{2,x}$ and $A_{2,y}$ as the excluded volume values, $$A_{2,X} = \frac{16\pi N_A r^3_X}{3M^2_X}, A_{2,Y} = \frac{16\pi N_A r^3_Y}{3M^2_Y},$$

based on said estimated values of molecular radii.

17. The method of claim 15 further comprising the steps of
a. determining the hydrodynamic radii of said macromolecules in solution by means of dynamic light scattering, differential viscometry or similar experimental techniques:,
b. estimating the values of the molecular radii $r_x$ and $r_y$ corresponding to said determined hydrodynamic radii; and
c. estimating $A_{2,x}$ and $A_{2,y}$ as the excluded volume values, $$A_{2,X} = \frac{16\pi N_A r^3_X}{3M^2_X}, A_{2,Y} = \frac{16\pi N_A r^3_Y}{3M^2_Y},$$

based on said estimated values of molecular radii.

18. The method of claim 15 further comprising the step of assuming said mean square radii of complexes of said macromolecules in solution are $<\lambda/70$, where $\lambda$ is the wavelength of said light beam of said light scattering photometer, and thereby the angular dependence of said intensity of scattered light may be ignored, and therefore said intensity may be measured at only one angle, $P(\theta)=1$, and therefore the $\langle r_g^2\rangle_{ij}$ are set to zero in the denominator of $R(c_f, \theta)$ for all ij.

19. The method of claim 15 further comprising the step of assuming said mean square radii of complexes of said macromolecules in solution are $<\lambda/70$, where $\lambda$ is the wavelength of said light beam of said light scattering photometer, and thereby the angular dependence of said intensity of scattered light may be ignored, and therefore said intensity may be measured at only one angle, $P(\theta)=1$, and therefore $\langle r_g^2\rangle_{ij}$ terms are considered negligible and therefore are set to zero in the numerator and the denominator of $R(c_f, \theta)$ for all ij.

20. The method of claim 15 wherein said aliquots are prepared manually and introduced to the detectors by means of scintillation vials.

21. The method of claim 15 wherein said aliquots are prepared manually and introduced to the detectors by means of a pump.

22. The method of claim 15 wherein said aliquots are prepared and introduced to the detectors automatically by means of a triple pump drawing on stock solutions of molecules X and Y at the highest required concentrations, and solvent; mixing these solutions to the required compositions; and subsequently delivering the aliquots to the detectors.

23. The method of claim 15 wherein said determining of said compositions consists of:
a. placing a concentration detector in-line with the light scattering photometer;

b. injecting a composition aliquot of sufficient volume so as to fill the flow cells of both the light scattering photometer and the concentration detector;

c. detecting the signal from said concentration detector; and d. converting the signal to composition $[c^x_f, c^Y_f]$ based on the known response factor of the macromolecules and their ratio as defined by the mixing procedure.

24. The method of claim 15 wherein said determining of said compositions consists of:

a. placing a concentration detector in-line with the light scattering photometer, wherein the concentration detector is sensitive to two independent properties of the molecules;

b. injecting a composition aliquot of sufficient volume so as to fill the flow cells of both the light scattering photometer and the concentration detector;

c. detecting the signals from said concentration detector; and d. converting the signals to composition $[c^x_f, c^Y_f]$ based on the known response factors of the macromolecules to said independent properties.

25. The method of claim 24 wherein said concentration detector is sensitive to spectral absorbance at two different wavelengths.

26. The method of claim 24 wherein said concentration detector is sensitive to spectral absorbance at one wavelength and refractive increment.

27. The method of claim 15 wherein said determining of said compositions consists of a. measuring each high concentration solution in a concentration detector; and b. calculating the compositions $[c^x_f, c^Y_f]$ of each composition aliquot from the parameters of the aliquot mixing procedure.

28. The method of claim 15 wherein said concentration detector comprises a UV/Visible light absorbance photometer, and said response factors are the absorption coefficients.

29. The method of claim 15 wherein said concentration detector comprises a differential refractometer, and said response factors are the refractive increments.

30. The method of claim 15 wherein said representations of said excess Rayleigh ratios are fitted to said equations of an association model by means of a Levenberg-Marquardt nonlinear least-squares fit.

* * * * *